United States Patent [19]

Maki et al.

[11] Patent Number: 4,490,292
[45] Date of Patent: Dec. 25, 1984

[54] 1,5-BENZOTHIAZEPINE DERIVATIVES AND PRODUCTION THEREOF

[75] Inventors: Yoshifumi Maki, Gifu; Magoichi Sako, Seki; Naomichi Mitsumori, Himeji; Sadayuki Maeda, Osaka; Masahiro Takaya, Yasu, all of Japan

[73] Assignee: Hamari Chemicals, Ltd., Osaka, Japan

[21] Appl. No.: 540,000

[22] Filed: Oct. 7, 1983

[51] Int. Cl.$^3$ .............................................. C07D 281/02
[52] U.S. Cl. .............................. 260/239.3 B; 424/275
[58] Field of Search .................. 260/239.3 B; 424/275

[56] References Cited

U.S. PATENT DOCUMENTS 4,416,819 11/1983 Nagao et al. ............... 260/239.3 B

OTHER PUBLICATIONS

Maki et al., "J. Chem. Soc.", Chemical Communications, (1983), pp. 450–451.

Primary Examiner—Robert T. Bond
Attorney, Agent, or Firm—Burgess, Ryan & Wayne

[57] ABSTRACT

Novel 1,5-benzothiazepine derivatives having the formula;

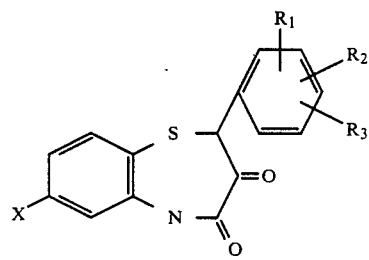

(wherein $R_1$, $R_2$ and $R_3$ each denotes hydrogen, a halogen, a lower alkyl group, a lower alkoxy group or a hydroxy group; $R_4$ denotes a lower alkyl group, an allyl group, a lower alkoxyalkyl group, a lower alkyl group substituted with a hydroxy group or a halogen, a lower alkylaminoalkyl group or a morpholino lower alkyl group; X denotes a halogen or hydrogen) are produced from corresponding 1,4-benzothiazine by a ring expansion reaction with trimethylhalosilane, hydrogen peroxide and water. The derivatives have analgesic, antipyretic and antiarrythmic activities.

9 Claims, No Drawings

1,5-BENZOTHIAZEPINE DERIVATIVES AND PRODUCTION THEREOF

This invention relates to novel benzothiazepine derivatives and a method for producing the same.

More particularly, the derivatives of this invention are 2-phenyl-(or substituted phenyl-)2,3-dihydro-5-substituted-1,5-benzothiazepine-3,4(5H)-dione which can be represented by the following formula:

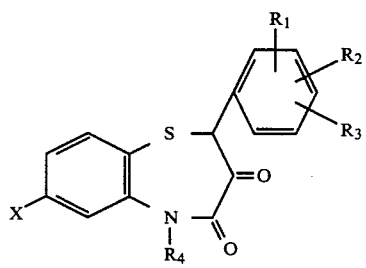

(wherein $R_1$, $R_2$ and $R_3$ each denotes hydrogen, a halogen, a lower alkyl group, a lower alkoxy group or a hydroxy group; $R_4$ denotes a lower alkyl group, an allyl group, a lower alkoxy-alkyl group, a lower alkyl group substituted with a hydroxy group or a halogen, a lower alkylaminoalkyl group or a morholino lower alkyl group; X denotes a halogen or hydrogen) and acid salts thereof.

Benzothiazepine derivatives are very interesting compounds, because it is known that some of them have several pharmacological activities.

The compound (I) of this invention belongs to novel benzothiazepine derivatives having two carbonyl groups in the thiazepine ring which is entirely unknown so far. The compound has excellent pharmacological effects such as analgesic, anti-pyretic or antiarrythmic activities and is useful as a mdeicine.

The compound (I) may be produced, for example, by the following synthesis route:

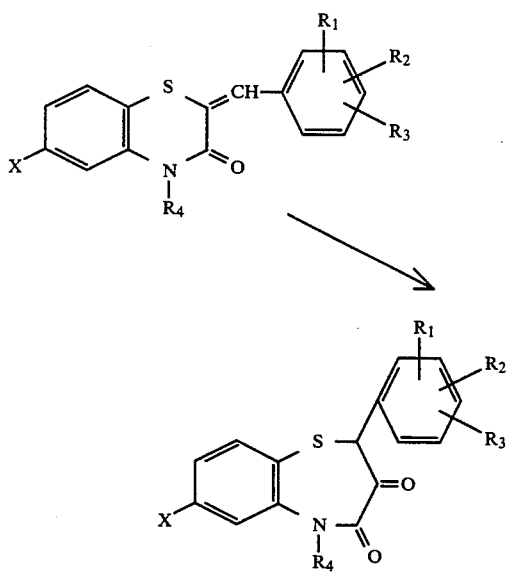

(wherein $R_1$, $R_2$, $R_3$, $R_4$ and X have the same meaning as above).

As illustrated in the above scheme, the benzothiazine ring of the compound (II) expands to a benzothiazepine ring by reacting 2-phenyl-(or substituted phenyl-)methylidene-4-substituted-2H-1,4-benzothiazine-3(4H)-one (II) with trimethylhalosilane, hydrogen peroxide and water, thereby the compound (I) is produced in a high yield. The reaction can be carried out in a non-reactive solvent such as methylene chloride or chloroform under cooling or at room temperature and it proceeds to completion in a period from scores of minute to several hours.

From the resulted reaction mixture, the compound (I) may be purified by a conventional procedure, for example, extraction with a solvent, recrystallization, column chromatography and treatment with activated carbon.

The starting compound (II) can easily be synthesized according to known methods described in V. Baligh and T. Rangarajan, J. Chem. Soc., 1980, 4703; J. Krapcho and C. F. Turk, J. Med. Chem., 1973, 16, 776.

Among the compounds (I) thus obtained, a compound having a nitrogen-containing substituent at 5-position of the benzothiazepine ring can be converted, if desired, to an inorganic acid salt such as hydrochloride, hydrobromide, sulfate, nitrate, etc., or an organic acid salt such as methanesulfonate, succinate, maleate, tartrate, etc. by a known method.

The ring-expansion of a heterocyclic compound is known in very rare cases, and there is no report from other inventor(s) so far on a ring-expansion from the six membered ring of benzothiazine to the seven membered ring the benzothiazepine having two carbonyl groups. Therefore, our invention is the first case on the latter ring-expansion.

The ring-expansion of this invention is useful for production of a medicine or an intermediate thereof, because it can be applied to the production of other benzothiazepine derivatives. The compound (I) of this invention can be employed as an analgetic, antipyretic or antiarrythmic agent, which may be administered at a daily dose level of 30 to 2,000 mg per kilogram body weight in 3 to 4 installments daily. It may be administered orally or parenterally in varied dosage form such as powder, granules, tablets, capsules, injection, suppository and cartilage.

In the case of powder, granules, tablets or capsules, the compound (I) may be used, for example, in admixture with pharmacologically acceptable excipients such as starch, lactose, sucrose and calcium carbonate; binders such as starch, carboxymethyl-cellulose and crystalline cellulose; and lubricants such as talc, etc.

Where the compound (I) is used as an injection, the carrier may, for example, be distilled water or physiological saline. Some pharmacological data and production procedure of the compound (I) are described in the following Experiment and Examples:

Experiment.

Pharmacology of 2-(4-methoxyphenyl)-2,3-dihydro-5-(2-dimethylaminoethyl)-1,5-benzothiazepine-3,4(5H)-dione (Ia) hydrochloride.

(1) Minimum Lethal Dose Test in Mice

Groups of 2 mice each, weighing 29–36 g, were treated intraperitoneally with the compound and observed for signs of - central, autaonomic and toxic responses for 5 hours. Mortality counts were made on days 0, 1 and 2 (day 0 is the dosing day). The results are shown in Table I.

TABLE I

Minimum Lethal Dose Test in Mice
Mortality and Minimum Acute Intraperitoneal Lethal Dose

| Route | Compound | Dose (mg/kg) | No. of Animals | No. of dead Animals Day of test | | | | Minimum Acute Lethal Dose (mg/kg) |
|---|---|---|---|---|---|---|---|---|
| | | | | 0 | 1 | 2 | Total | |
| I.P. | Vehicle | 0 | 2 | 0 | 0 | 0 | 0 | — |
| | Ia | 10 | 2 | 0 | 0 | 0 | 0 | 300 |
| | | 30 | 2 | 0 | 0 | 0 | 0 | |
| | | 100 | 2 | 0 | 0 | 0 | 0 | |
| | | 300 | 2 | 2 | — | — | 2 | |

(2) Analgestic Activity (Mouse Anti-Writhing Method)

Groups of 5 mice each, weighing 26–32 g, were treated intraperitoneally with the compounds. The method is based on the antagonism of a writhing syndrome (abnormal contraction and twisting of the body) produced by the intraperitoneal injection of 10 ml/kg of 0.7% acetic acid-saline solution. Ten minutes after the acetic acid injection, the number of writhes observed in a 10 minute counting period was recorded. The compound was administered 45 minutes before the acetic acid injection. The results are shown in Table II.

TABLE II

Mouse Anti-Writhing Method

| Route | Compound | Dose (mg/kg) | No. of Animals | No. of Writhes (Mean + S.D.) | % Change from Control |
|---|---|---|---|---|---|
| I.P. | Vehicle | 0 | 10 | 10.9 ± 8.9 | — |
| | Ia | 60 | 5 | 0.8 ± 1.3** | −92.7 |
| | Pentazocine | 30 | 5 | 1.8 ± 2.2* | −83.5 |
| | Vehicle | 0 | 5 | 12.8 ± 6.3 | — |
| | Ia | 60 | 5 | 0.0 ± 0.0** | −100.0 |

*: $P \leq 0.05$ as compared to the vehicle group
**: $P \leq 0.04$ as compared to the vehicle group

(3) Anit-pyretic Activity (Temperature Regulation in Pyretic Rats)

Rats, weighing 220–300 g, were treated subcutaneously in the nape of the neck with 6 ml of 40% suspension of dried Brewer's yeast in distilled water. Groups of 3 rats were treated intraperitoneally with the compound 17 hours challenge. Rectaltemperature were recorded with a thermister type thermometer (Type BMA-77 produced by Natsume Seisalusho, Japan) just prior to the drug administration and at 30 minutes intervals for 2 hours. The results are shown in Table III.

TABLE III

Effect on Yeast-induced Pyresis in Rats

Rectal Temperature (C.°, Mean + S.D.)

| Route | Compound | Dose (mg/kg) | No. of Animals | Time after Treatment (hour) | | | | | Average at 0.5–2.0 Hours Post-treatment | Change C.° |
|---|---|---|---|---|---|---|---|---|---|---|
| | | | | 0 | 0.5 | 1.0 | 1.5 | 2.0 | | |
| L.P. | Vehicle | 0 | 3 | 39.6 ± 0.25 | 39.9 ± 0.23 | 39.9 ± 0.15 | 39.7 ± 0.07 | 39.6 ± 0.09 | 39.8 | 0 |
| | Ia | 60 | 3 | 39.7 ± 0.15 | 38.4 ± 0.57 | 38.4 ± 0.35 | 38.8 ± 0.49 | 39.0 ± 0.51 | 38.7 | −1.1 |
| | Amino- | 30 | 3 | 39.6 ± 0.10 | 38.1 ± 0.50 | 37.2 ± 0.58 | 37.2 ± 0.53 | 37.4 ± 0.46 | 37.5 | −2.3 |
| | Normal Rat | | 4 | | | | | 37.3 ± 0.12 | | |

EXAMPLE 1

To a solution of sodium ethoxide previously prepared from sodium (8.7 g) and absolute ethanol (350 ml), was added 5-chloro-2-benzothiazolinone (70.0 g) with sitirring.

To this clear solution, methyl iodide (80.3 g) was added dropwise and then the mixture was refluxed for three hours. After removal of the solvent under reduced pressure, the residual oil was treated with water. The resulted precipitates was collected on a filter, washed with water, and air-dried to give 5-chloro-3-methyl-2-benzothiazolinone (73.4 g) as needles. m.p. 106.0–107.5° C.

5-Chloro-3-methyl-2-benzothiazolinone (70.0 g) was added to a mixture of water (118 ml), ethanol (350 ml) and potassium hydroxide (78.6 g). The solution was refluxed with stirring for three hours. After the solvent was evaporated under reduced pressure, the residual oil was dissolved in water. After removal of insoluble yellow crystals by filtration, the filtrate was neutralized with 2N-acetic acid, then resulting oily substance was extracted with ethyl acetate. The extract was washed with water, dried ($Na_2SO_4$), and evaporated to give oily 4-chloro-2-methylaminothiophenol (59.7 g). To a solution of sodium hydroxide (14.0 g) in water (100 ml) was added 4-chloro-2-methylaminothiophenol (59.6 g) with stirring, and then was added dropwise a solution of chloroacetic acid (34.0 g) in water (50 ml) at 20–25° C., followed by heating almost to boiling for three hours.

After the reaction mixture was cooled to room temperature, resulted light yellow precipitates were filtered off, washed with water, and air-dried to give 6-chloro-4-methyl-2H-1,4-benzothiazine-3(4H)-one (68.7 g) as prisms. m.p. 119.0–121.0° C.

To a solution of sodium ethoxide previously prepared from sodium (0.94 g) and absolute ethanol (55 ml), were added 6-chloro-4-methyl-1,4-benzothiazine-3(4H)-one (8 g) and anisaldehyde (5.1 g).

The mixture was then refluxed with stirring for one hour. After cooling, the reaction mixture was diluted with water (25 ml). the resulting precipitated products were collected by suction and recrystallized from methanol to give 6-2(4-methoxyphenylmethylidene)-4-methyl-2H-1,4-benzothiazine-3(4H)-one (4.2 g) as yellow powder. m.p. 136–138° C. Anal. Calcd. for $C_{17}H_{14}NO_2SCl$: C, 61.54; H, 4.25; N, 4.22 /Found: C, 61.35; H, 4.20; N, 4.25.

IR(KBr)cm$^{-1}$: 1626, 1578.

NMR(CDCl$_3$)ppm: 3.46(s,3H), 3.81(s,3H), 6.53–7.67(br., 7H), 7.77(s,1H).

To a stirred solution of 6-chloro-2-(4-methoxy phenylmethylidene)-4-methyl-2H-1,4-benzothiazine-3(4H)-one (1.0 g) in chloroform (30 ml) were added dropwise chlorotrimethylsilane (1.14 g) followed by 30% hydroperoxide (0.54 g) at −5° C. After stirring at −5° C. for two hours, water was added and then the stirring was continued for two hours at room temperature. The resulting solution was diluted with chloroform, washed with saturated aqueous sodium bicarbonate, dried (Na₂SO₄), and evaporated under reduced pressure.

The residual oil was purified by column chromatography on a silica gel (n-hexane-benzene (1:1)) to give oily 7-chloro-2-(4-methoxyphenyl)-2,3-dihydro-5-methyl-1,5-benzothiazepine-3,4-(5H)-dione (0.65 g).

Anal. Calcd. for $C_{17}H_{14}NO_3SCl$: C, 58.70; H, 4.06; N, 4.03. Found: C, 58.51; H, 4.08; N, 3.98.

IR(Neat)cm⁻¹: 1722, 1683, 1604, 1572, 1511.

NMR(CDCl₃)ppm: 3.44(s,3H), 3.76(s, 3H), 5.41(s, 1H), 6.65–7.69(m, 7H).

EXAMPLE 2

To a solution of sodium ethoxide, previously prepared from sodium (8.7 g) and absolute ethanol (350 ml) was added 5-chloro-2-benzothiazolinone (70.0 g) with stirring. To the clear solution thus obtained, was added dropwise N,N-dimethylaminoethylchloride (61.0 g), and the mixture was refluxed for three hours.

After removal of the solvent under reduced pressure, the residue was dissolved in ethylacetate, and the solution was washed with aqueous sodium hydroxide. The ethylacetate extract was acidified with dilute hydrochloric acid and the aqueous layer was neutralized with saturated aqueous sodium bicarbonate and then the resulting oily substance was extracted with ethylacetate. The extract was washed with water, dried (Na₂SO₄) and evaporated to give 5-chloro-3-(2-dimethylaminoethyl)-2-benzothiazolinone (74.5 g) as prisms. m.p. 62.5–65.5° C. 5-Chloro-3-(2-dimethylaminoethyl)-2-benzothiazolinone (74.5 g) was added to a mixture of water (110 ml), ethanol (350 ml) and potassium hydroxide (75.0 g). The solution was refluxed with stirring for two hours. After removal of the solvent under reduced pressure, the residual oil was dissolved in water, then the aqueous solution was washed with ether. The aqueous layer was washed and neutralized with 2N-acetic acid with weak stirring. The resulting light yellow precipitates were collected on a filter, washed with water and air-dried to give 4-chloro-2-(2-dimethylaminoethylamino)-thiophenol (52.9 g) as prisms. m.p. 126–130° C.

To a solution of sodium hydroxide (9.04 g) in water (130 ml) was added 4-chloro-2-(2-dimethylaminoethylamino)-thiophenol (50.0 g) with stirring.

To the clear solution thus obtained, a solution of chloroacetic acid (20.5 g) in water (30 ml) was added dropwise at a temperature below 20° C., then the mixture was heated to gentle boiling for one hour.

This mixture was cooled to 40° C., and then added with conc. hydrochloric acid (18 ml), slowly.

After refluxing for further four hours, the reaction mixture was made alkaline with aqueous potassium hydroxide and extracted with ethylacetate. Tha extract was washed with water, dried (Na₂SO₄) and evaporated to give oily 6-chloro-4-(2-dimethylaminoethyl)-2H-1,4-benzothiazine-3(4H)-one (41.0 g).

To a solution of sodiulm ethoxide, previously preapared from sodium (0.76 g) and absolute ethanol (60.0 ml) were added 6-chloro-4-(2-dimethylaminoethyl)-2H-1,4-benzothiazine-3(4H)-one (8.0 g) and anisaldehyde (4.8 g).

The mixture was refluxed with stirring for one hour. After cooling, the reaction mixture was acidified with dilute hydrochloric acid and concentrated under reduced pressure. The resulting oily substance was extracted with chloroform. The extract was washed with a small amount of water, dried (Na₂SO₄) and evaporated. The residue soon solidified which was recrystallized from iso-propyl alcohol to give 6-chloro-2-(4-methoxyphenylmethylidene)-4-(2-dimethylaminoethyl)-2H-1,4-benzothiazine-3(4H)-one (4.3 g) hydrochloride as yellow plates. m.p. 196.0–230.5° C.

Anal. Calcd. for $C_{20}H_{21}N_2O_2SCl \cdot HCl$: C, 56.47; H, 5.21; N, 6.59. Found: C, 56.30; H, 5.23; N, 6.70.

IR(KBr)cm⁻¹: 2580, 2425, 1638, 1598, 1578, 1503.

NMR(CDCl₃)ppm: 2.86(s, 6H), 3.10–3.60(br., 2H), 3.80(s, 3H), 4.20–4.64(br., 2H), 6.64–7.68(m, 7H), 7.69(s, 1H).

To a stirred suspension of 6-chloro-2-(4-methoxyphenylmethylidene)-4-(2-dimethylaminoethyl)-2H-1,4-benzothiazine-3(4H)-one (2.0 g) in chloroform (30 ml) were added dropwise chlorotrimethylsilane (1.79) followed by 30% hydroperoxide (0.83 g) at −5° C. The mixture was stirred for two hours at the same temperature. After water (2.7 ml) was added to the mixture, its temperature was raised to room temperature and then the stirring was continued for another two hours.

The resulting solution was diluted with chloroform, washed with saturated aqueous sodium bicarbonate, dried (Na₂SO₄), and evaporated under reduced pressure. The redidual oil was purified by column chromatography on silica gel (chloroform-ethanol (30:1)) to give oily 7-chloro-2-(4-methoxyphenyl)-2,3-dihydro-5-(2-dimethylaminoethyl)-1,5-benzothiazepine-3,4(5H)-dione (1.2 g).

Anal. Calcd. for $C_{20}H_{21}N_2O_3SCl$: C, 59.33; H, 5.23; N, 6.92. Found: C, 58.85; H, 5.25; N, 6.88.

IR(Neat)cm⁻¹: 2825, 2760, 1726, 1665, 1609, 1578, 1511.

NMR(CDCl₃–D₂O)ppm: 2.39(s, 6H), 2.39–2.75(br., 2H), 3.74(s, 3H), 3.83–4.27(br., 2H), 6.55–7.67(m, 7H).

In the same manner as described in Example 2, the following compounds were obtained:

7-Chloro-2--phenyl-2,3-dihydro-5-(2-dimethylaminoethyl)-1,5-benzothiazepine-3,4(5H)-dione:

Anal. Calcd. for $C_{19}H_{19}N_2O_2SCl$: C, 60.87; H, 5.11; N, 7.47. Found: C, 61.03; H, 5.02; N, 7.45.

IR(Neat)cm⁻¹:2810, 2760, 1721, 1660, 1576.

NMR(CDCl₃-D₂O)ppm: 2.22(s, 6H), 2.41–2.78(br., 2H), 3.58–4.34(br., b 2H), 6.70–7.74(m, 8H).

7-Chloro-2-(4-chlorophenyl)-2,3-dihydro-5-(2-dimethylaminoethyl)-1,5-benzothiazepine-3,4(5H)-dione:

Anal. Calcd. for $C_{19}H_{18}N_2O_2SCl_2$: C, 55.75; H, 4.43; N, 6.84. Found: C, 55.10; H, 4.53; N, 6.77.

IR(Neat)cm⁻¹: 2805, 2760, 1718, 1660, 1573.

NMR(CDCl₃-D₂O)ppm: 2.21(s, 6H), 2.39–2.84(br., 2H), 3.44–4.28(br., 2H), 6.50–7.56(m, 7H).

7-Chloro-2-(3,4-dimethoxyphenyl)-2,3-dihydro-5-(2-dimethylaminoethyl)-1,5-benzothiazepine-3,4(5H)-dione:

Anal. Calcd. for $C_{21}H_{23}N_2O_4SCl$: C, 57.99; H, 5.33; N, 6.44. Found: C, 58.10; H, 5.28; H, 6.35.

IR(Neat)cm⁻¹: 2810, 2760, 1722, 1661, 1578.

NMR(CDCl₃-D₂O)ppm: 2.23(s, 6H), 2.43–283(br., 2H), 3.40–4.32(br., 2H), 3.83(s, 6H), 6.40–7.72(m, 6H).

7-Chloro-2-(3,4,5-trimethoxyphenyl)-2,3-dihydro-5-(2-dimethylaminoethyl)-1,5-benzothiazepine-3,4(5H)-dione:

Anal. Calcd. for $C_{22}H_{25}N_2O_5SCl$: C, 56.83; H, 5.42; N, 6.02. Found: C, 56.90; H, 5.40; N, 5.98.

IR(Neat)cm⁻¹; 2810, 2760, 1725, 1660, 1575.

NMR(CDCl₃-D₂O)ppm: 2.25(s, 6H), 2.42–2.81(br., 2H), 3.37–4.37(br., 2H, 3.88(s, 9H), 6.49–7.77(m, 5H).

7-Chloro-2-(4-methoxyphenyl)-2,3-dihydro-5-(3-dimethylaminopropyl)-1,5-benzothiazepine-3,4(5H)-dione:

Anal. Calcd. for $C_{21}H_{23}N_2O_3SCl$: C, 60.21; H, 5.53; N, 6.69. Found: C, 60.20; H, 5.49; N, 6.55.

IR(Neat)cm$^{-1}$: 2805, 2755, 1720, 1663, 1603, 1576.

NMR(CDCl$_3$-D$_2$O)ppm: 1.43–2.67(br., 4H), 2.20(s, 6H), 3.63–4.31(br., 2H), 3.71(s, 3H), 6.55–7.75)m, 7H).

7-Chloro-2-(4-methoxyphenyl)-2,3-dihydro-5-(2-morphorinoethyl)-1,5-benzothiazepine-3,4(5H)-dione:

Anal. Calcd. for $C_{22}H_{23}N_2O_4SCl$: C, 59.12; H, 5.19; N, 6.27. Found: C, 58.83; H, 5.20; N, 6.22.

IR(Neat)cm$^{-1}$: 2880, 2759, 1720, 1660, 1603, 1574.

NMR(CDCl$_3$-D$_2$O)ppm: 2.07–2.87(br., 6H), 3.15–4.35(br., 6H), 3.75(s, 3H), 6.43–7.77(m, 7H).

EXAMPLE 3.

A solution of 2H-1,4-benzothiazine-3(4H-one (2 g) and 4-chlorobenzaldehyde (2.6 g) in dimethylformamide (15 ml) was treated with sodium methylate (0.98 g). The temperature of the mixture rose spontaneously. After cooling to room temperature, the reaction mixture was stirred and heated at 110° C. with a continuous removal of a low boiling substance for 3 hours. The reaction mixture was cooled to 30° C., and poured onto 100 ml of iced water. The resulted yellow solid was filtered and recrystallized from a mixture of dimethylformamide and isopropyl alcohol. 2-(4-Chlorophenylmethylidene)-2H-1,4-benzothiazine-3(4H)-one (3.3 g) was obtained as yellow crystals. m.p. 245–248° C.

In a similar manner as described in Example 3, the following compounds were obtained:

2-(4-Methylphenyl)methylidene-2H-1,4-benzothiazine-3(4H)-one, m.p. 266° to 274° C. (recrystallized from a mixture of dimethyl formamide and isopropyl alcohol);

2-(2,4-Dichlorophenyl-methylidene)-2H-1,4-benzothiazine-3(4H)-ne, m.p. 238° to 240° C.

IR(Nujol)cm$^{-1}$: 3160, 1660, 1580, 1550.

Anal. Calcd. for $C_{15}H_9OSNCl_2$: C, 62.85; H, 3.16; N, 4.78; Found: C, 62.88; H, 3.08; N, 4.78.

2-(3,4,5-Trimethoxyphenylmethylidene)-2H-1,4-benzothiazine- 3(4H)-one, m.p. 204° to 205° C.

Anal. Calcd. for $C_{18}H_{17}O_4SN$: C, 62.97; H, 4.99; N, 4.08. Found: C, 62.89; H, 5.02; N, 4.18.

IR(Nujol)cm$^{-1}$: 3150, 1650, 1585.

EXAMPLE 4

2-(4-Chlorophenylmethylidene)-2H-1,4-benzothiazine-3(4H)-one (2.0 g) was reacted with sodium hydroxide (0.72 g) in methyl ethyl ketone (20 ml) at 80° C. for 30 minutes. After the solution turned clear, it was cooled to room temperature. N-(2-chloroethyl)morpholine hydrochloride (1.7 g) was added to the mixture. The organic solvent was evaporated under reduced pressure. The resulted yellow solid was filtered and washed with water and with methanol. It was recrystallized from a mixture of dimethylformamide and isopropyl alcohol. 2-(4-Chlorophenyl)-methylidene-4-(2-morpholinoethyl)-2H-1,4-benzothiazine-3(4H)-one (2.0 g) was obtained as yellow crystals, m.p. 173° to 175° C.

Anal. Calcd. for $C_{21}H_{21}O_2SN_2Cl$: C, 62.91; H, 5.28; N;, 6.99. Found: C, 62.85; H;, 5.33; N, 7.22.

IR(Nujol)cm$^{-1}$: 1630, 1590, 1575.

NMR(CDCl$_3$)ppm: 2.56(t, 4H), 2.70(t, 2H), 3.70(t, 4H), 4.22(t, 2H), 6.86–7.60(m;, 8H), 7.72(s, 1H).

In a similar manner as described in Example 4, the following compounds were obtained:

2-(4-Methoxyphenylmethylidene)-4-(2-morpholinoethyl)-2H-1,4- benzothiazine-3(4H)one, m.p. 183° to 184° C. (recrystallized from tetrahydrofuran).

Anal. Calcd. for $C_{22}H_{24}O_3SN_2$: C, 66.65; H, 6.10; N, 7.07. Found: C, 66.65; H, 5.85; N, 7.07.

IR(Nujol)cm$^{-1}$: 1630, 1605, 1590.

NMR(CDCl$_3$)ppm: 2.56(t, 4H), 2.69(t, 2H), 3.68(t, 4H), 3.80(s, 3H), 4.20(t, 2H), 6.84–7.60(m, 8H), 7.74(s, 1H).

2-(4-Methylphenylmethylidene)-4-(2-morpholinoethyl)-2H-1,4-benzothiazine-3(4H)-one, m.p. 119° to 121° C. (recrystallized from a mixture of dimethylformamide and isopropyl alcohol).

Anal. Calcd. for $C_{22}H_{24}O_2SN_2$: C, 69.45; H, 6.36; N, 7.36. Found: C, 60.40; H, 6.33; N, 7.50.

IR(Nujol)cm$^{-1}$: 1640, 1590, 1580, 1560.

NMR(CDCl$_3$ppm: 2.38(s, 3H), 2.55(t;, 4H), 2.73(t, 2H), 3.72(t, 4H, 4.25(t, 2H), 6.92–7.60(m, 8H), 7.80(s, 1H).

2-(2,4-Dichlorophenylmethylidene)-4-(2-morpholinoethyl)-2H-1,4-benzothiazine-3(4H)-one, m.p. 169° to 173° C. (recrystallized from a mixture of dimethylformamide and methanol).

Anal. Calcd. for $C_{21}H_{20}O_2SN_2Cl_2$: C, 57.93; H, 4.63; N, 6.43 Found: C, 58.04; H, 4.55; N, 6.50.

IR(nujol)cm$^{-1}$: 1645, 1590, 1580.

NMR(CDCl$_3$)ppm: 2.36(t, 4H), 2.70(t;, 2H), 3.68(t, 4H), 4.22(t, 2H), 6.82–7.50(m, 7H), 7.86(s, 1H).

2-(3, 4, 5-Trimethoxyphenylmethylidene)-4-(2-morpholinoethyl)-2H-1,4-benzothiazine-3(4H)-one, m.p. 138° to 139° C.

Anal. Calcd. for $C_{24}H_{28}O_5SN_2$: C, 63.14; H, 6.18; N, 6.14. Found: C, 63.26; H, 6.08; N, 6.22.

IR(Nujol)cm$^{-1}$: 1640, 1595, 1575.

NMR(CDCl$_3$)ppm: 2.58(t, 4HO, 2.76(t, 2H), 3.74(t, 4H), 3.88(s, 3H), 3.90(s, 3H), 3.92(s, 3H), 4.26(t, 2H), 6.68–7.38(m, 6H), 8.00(s, 1H).

EXAMPLE 5

2-(2,4-Dichlorophenylmethylidene)-2H-1,4-benzothiazine-3(4H)-one (3.0 g) in methyl ethyl ketone (10 ml) was treated with sodium hydroxide (0.98 g) at 80° C. for 30 minutes. The reaction mixture was cooled to room temperature and added with dimethylaminoethyl chloride (1.7 g), refluxed for 3 hours and cooled to 30° C. The organic layer was washed with 20 ml of water two times, dried and evaporated under reduced pressure. The residue was dissolved in 20 ml of isopropyl alcohol and added with 0.9 ml of conc. HCl. The resulted precipitates were filtered and recrystallized from 30 ml of isopropyl alcohol to give 2-(2,4-Dichlorophenylmethylidene)-4-(2-dimethylaminoethyl)-2H-1,4-benzothiazine hydrochloride as yellow crystals. m.p. 238° to 242° C.

Anal. Calcd. for $C_{19}H_{19}OSN_2Cl_3$: C, 53.10; H, 4.46; N, 6.52; Found: C, 53.25; H, 4.55; N, 6.40.

IR(Nujol)cm$^{-1}$: 2670, 1635, 1585, 1570, 1560.

NMR(DMSO-d$_6$)ppm: 2.92(s, 6H), 3.44(t, 2H), 4.54(t, 3H), 6.96–7.66(m, 7H), 7.84(s, 1H).

EXAMPLE 6

2-(3,4,5-Trimethoxyphenylmethylidene)-4-(2-mophlinoethyl)-1,4-benzothiazine-3(4H)-one (0.5 g) was dissolved in 5 ml of chloroform. Chlorotrimethylsilane (1 ml) was added thereto. The mixture was stirred for 30 min. at room temperature and cooled below 0° C. Another 1 ml of trimethylchlorosilane was added and then 30% hydrogen peroxide (0.26 g) was added dropwise for 30 minutes, while the temperature of the mixture maintained below 0° C. Water (1 ml) was added to the solution. The reaction was completed after stirring at room temperature for 2 hours. The organic phase was washed with an aqueous solution of sodium bicarbonate, and with water two times. The organic layer was separated, dried and evaporated under reduced pressure. The residue was purified by silicagel chromatography. 2-(3,4,5-Trimethoxyphenyl)-5-(2-morpholinoethyl)- 2,3-dihydro-1,5-benzothiazepine-3,4(5H)-dione (0.25 g) was obtained as oil.

Anal. Calcd. for $C_{24}H_{28}O_6SN_2$: C, 61.01; H, 5.97; N, 5.93. Found: C, 61.25; H, 6.11; N, 6.08.

IR(Neat)cm$^{-1}$: 3290, 1725, 1665, 1590.

NMR(CDCl$_3$)ppm: 2.42(t, 4H), 2.60(t, 2H), 3.60(t, 4H), 3.76–3.88(m, 9H), 4,02(t, 2H), 5.96(s, 1H), 6.52–7.40(m, 6H).

In a similar manner as described in Example 6, the following compounds were prepared:

2-(4-Chlorophenyl)-5-(2-morpholinoethyl)-2,3-dihydro-1,5-benzothiazepine-3,4(5H)-dione as oil.

Anal. Calcd. for $C_{21}H_{21}O_3SN_2Cl$: C, 60.50; h, 5.08; N, 6.72. Found: C, 60.61; H, 5.02; N, 6.68.

IR(Neat)cm$^{-1}$: 3300, 1730, 1670, 1585.

NMR(CDCl$_3$)ppm: 2.42(t,m, 4H), 2.58(t, 2H), 3.58(t, 4H), 4.12(t, 2H), 5.54(s, 1H), 6.82–7.78(m, 8H).

2-(4-Methylphenyl)-5-(2-morpholinoethyl)-2,3-dihydro-1,5-benzothiazepine-3,4(5H)-dione as oil.

Anal. Calcd. for $C_{22}H_{24}O_3SN_2$: C, 66.65; H, 6.10; N. 7.07. Found: C, 66.48; H, 6.10; N, 7.10.

IR(Neat)cm$^{-1}$: 3300, 1720, 1680, 1590.

NMR(CDCl$_3$)ppm: 2.26(s, 3H), 2.48(t, 4H), 2.59(t, 2H), 3.56(t, 4H), 4.05(m, 2H), 5.80(s, 1H), 6.90–7.68(m, 8H).

2-(4Methoxyphenyl)-5-(2-morpholinoethyl)-2,3-dihydro-1,5-benzothiazepine-3,4(5H)-dione as oil.

Anal. Calcd. for $C_{22}H_{24}O_4SN_2$: C, 64.06; H, 5.87; N, 6.21; Found: C, 64.21; H, 5.67; N, 6.00.

IR(Neat)cm$^{-1}$: 3290, 1730, 1660, 1600, 1585.

NMR(CDCl$_3$)ppm: 2.42(t, 4H), 2.56(t, 2H), 3.58(t, 4H), 3.72(s, 3H), 4.10(t, 2H), 5.40(s, 1H), 6.72–7.48(m, 8H).

2-(2,4-Dichlorophenyl)-5-(2-morpholinoethyl)-2,3-dihydro-1,5-benzothiazepine-3,4(5H)-dione as oil.

Anal. Calcd. for $C_{21}H_{20}O_3SN_2Cl_2$: C, 55.88; H, 4.47; N, 6.21. Found: C, 56.01; H, 4.43; N, 6.11.

IR(Neat)cm$^{-1}$: 3150, 1720, 1660, 1580.

NMR(CDCl$_3$)ppm: 2.36(t, 4H), 2.50(t, 2H), 3.54(t, 4H), 4.01(t, 2H), 6.04(s, 1H), 6.80–7.70(m, 7H).

EXAMPLE 7

The solution of 2-(2,4-dichlorophenylmethylidene)-4-(2-dimethylaminoethyl)-2H-1,4-benzothiazine-3(4H)-one hydrochloride (1 g) in 10 ml of chloroform was cooled below 0° C. and added with trimethylchlorosilane (2 ml), and then added with 30% hydrogen peroxide (0.29 g) for 30 minutes. The solution was stirred for 30 minutes below 0° C., and added with 1 ml of water. After further stirring for 1 hour at room temperature, 10 ml of water was added to the reaction mixture. The aqueous phase of the mixture was adjusted to a pH within 8–9 and the chloroform layer was separated from the mixture. The remaining aqueous phase was extracted with 10 ml of chloroform. The chloroform solutions wee combined, dried and evaporated under reduced pressure. The oily residue was purified by silicagel chromatography to give 2-(2,4-dichlorophenyl)-5-(2-dimethylaminoethyl)-2,3-dihydro-1,5-benzothiazepine-3,4(5H)-dione (1.0 g) as oil.

Anal. Calcd. for $C_{19}H_{18}O_2SN_2$: C, 55.75; H, 4.43; N, 6.84. Found: C, 55.77; H, 4.40; N, 6.78.

IR(Neat)cm$^{-1}$: 3200, 1735, 1655.

NMR(CDCl$_3$)ppm: 2.18(s, 6H), 2.46(t, 2H), 3.96(m, 2H), 6.84–7.54(m, 7H).

EXAMPLE 8

Chlorotrimethylsilane (19.5 g) was dropped, while stirring at $-5°$ C. for 30 minutes, into a solution of 2-(4-methoxymethylidene)-4-(2-dimethylaminoethyl)-2H-1,4-benzothiazine-3(4H)-one (20 g) in dichloromethane (300 ml). After further stirring at $-5°$ C. for 30 minutes, 10 ml of water was added and the reaction mixture was stirred at 23° C. for 2 hours. The resulted reaction mixture was diluted with 400 ml of saturated sodium chloride solution and the dichloromethane layer was separated, washed with a mixture of saturated sodium chloride solution (400 ml) and water (300 ml), dried over anhydrous magnesium sulfate and evaporated to remove the solvent. The residue was recrystallized from acetone to give 16.3 g of 2-(4-methoxyphenyl)-2,3-dihydro-5-(2-dimethylaminoethyl)-1,5-benzothiazepine-3,4(5H)-dione hydrochloride as colorless powder having a melting point from 198° to 201° C.

Anal. Calcd. for $C_{20}H_{22}N_2O_3S \cdot HCl$: C, 59.04; H, 5.65; N, 6.88. Found: C, 59.17; H, 5.68; N, 6.91.

IR(Nujol)cm$^{-1}$: 3350, 2670, 1650, 1638, 1600, 1580.

IR(KBr)cm$^{-1}$: 3400, 2670, 1720, 1660, 1610, 1585.

NMR(DMSO-d$_6$)ppm: 2.80(s, 6H), 3.36(br., 2H), 3.72(s, 3H), 4.42(br., 2H), 6.06(br., 1H), 6.40–7.90(m, 8H).

In a similar manner as described in Example 8, the following compounds were obtained:

2-Phenyl-2,3-dihydro-5-methyl-1,5-benzothiazepine-3,4(5H)-dione as oil.

Anal. Calcd. for $C_{16}H_{13}NO_2S$: C, 67.84; H, 4.63; N, 4.95. Found: C, 67.68; H;, 4.69; N, 5.07.

IR(Neat)cm$^{-1}$: 3300(br., weak), 1720, 1660, 1580.

NMR(CDCl$_3$)ppm: 3.45(s, 3H), 5.50(s, 1H), 7.05–7.60(m, 9H).

2-(4-Chlorophenyl)-2,3-dihydro-5-methyl-1,5-benzothiazepine-3,4-(5H)-dione as oil.

Anal. Calcd. for $C_{16}H_{12}NO_2SCL$: C, 60.47; H, 3.77; N, 4.40. Found: C, 60.78; H, 3.51; N, 4.26.

IR(Neat)cm$^{-1}$: 1675, 1580.

NMR(CDCl$_3$)ppm: 3.53(s, 3H), 5.12(s, 1H), 6.95–7.80(m, 8H).

2-(4-Methoxyphenyl)-2,3-dihydro-5-methoxymethyl-1,5-benzothiazepine-3,4-(5H)-dione, m.p. 124.5° to 125.5° C. (recrysatalized from ethanol).

Anal. Calcd. for $C_{18}H_{17}NO_4S$: C, 62.97; H, 4.99; N, 4.08. Found: C, 62.75; H, 4.93; N;, 4.06.

IR(Nujol)cm$^{-1}$: 1720, 1670, 1610, 1585.

NMR(CDCl$_3$)ppm: 3.54(s, 3H), 5.06(s, 1H), 5.42(q, 2H), 6.76–7.80(m, 8H).

2-(4-Methoxyphenyl)-2,3-dihydro-5-(2-hydroxyethyl)-1,5-benzothiazepine-dione as oil.

Anal. Calcd. for $C_{18}H_{17}NO_2S$: C, 62.97; H, 4.99; N, 4.08. Found: C, 63.141; H, 5.02; N, 3.97.

IR(Neat)cm$^{-1}$: 3425, 1725, 1660, 1610, 1585.

NMR(CDCL$_3$)ppm: 3.18(broad s, 1H), 3.80(s, 3H), 3.88–4.20(m, 4H), 5.50(broad s, 1H), 6.80–7.85(m, 8H).

2-(4-Methoxyphenyl)-2,3-dihydro-5-(2-chloroethyl)-1,5-benzothiazepine-3,4(5H)-dione as oil.

Anal. Calcd. for $C_{18}H_{16}NO_3SCl$: C, 59.75; H, 4.42; N;, 3.87. Found: C, 60.02; H, 4.38; N;, 3.77.

IR(Neat)cm$^{-1}$: 3350, 1725, 1660, 1600, 1580.
NMR(CDCl$_3$)ppm: 3.71(s, 3H), 4.10–4.60(m, 4H), 5.44(broad s, 1H), 6.76–8.46(m, 8H).

2-(4-Methoxyphenyl)-2,3-dichloro-5-(2-bromoethyl)-1,5-benzothiazepine-3,4-(5H)-dione as oil.

Anal. Calcd. for C$_{18}$H$_{16}$NO$_3$SBr: C, 53.20; H, 3.94; N, 3.44; Found: C, 53.47; H, 4.01; N, 3.50.

IR(Neat)cm$^{-1}$: 3350, 1720, 1660, 1600, 1580.
NMR(CDCl$_3$)ppm: 3.56(m, 2H), 3.76(s, 3H), 4.28(m, 2H), 5.42(broad s, 1H), 6.76–8.80(m, 8H).

We claim:

1. A benzothiazepine compound of the formula:

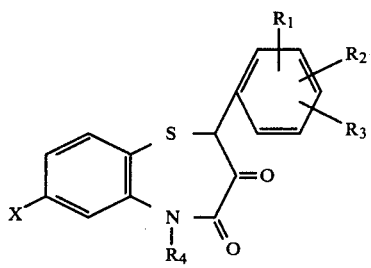

wherein R$_1$, R$_2$ and R$_3$ each independently denotes hydrogen, halogen, a lower alkyl group, a lower alkoxy group or a hydroxy group; R$_4$ denotes a lower alkyl group, an allyl group, a lower alkoxy-alkyl group, a lower alkyl group substituted with a hydroxy group or a halogen, a lower alkylaminoalkyl group or a morpholino lower alkyl group; X denotes a halogen or hydrogen, and an acid salt thereof.

2. A compound according to claim 1 wherein R$_1$, R$_2$ and R$_3$ each is hydrogen, chlorine, or a methyl or methoxy group; R$_4$ is a methyl, methoxymethyl, hydroxyethyl, chloroethyl, bromoethyl, dimethylaminoethyl, or morpholinoethyl group; X is hydrogen or chlorine.

3. A compound according to claim 1 wherein at least one of R$_1$, R$_2$ and R$_3$ is a methyl or methoxy group or chlorine and the remainder, if any, is a hydrogen; R$_4$ is methyl, methoxy-methyl, hydroxyethyl, chloroethyl, bromoethyl, dimethylaminoethyl or morpholinoethyl group; X is hydrogen or chlorine.

4. A compound according to claim 1 wherein R$_1$ is a methyl group, methoxy group or chlorine substituted on the 4-position of the phenyl group, and R$_2$ and R$_3$ each is hydrogen.

5. A compound according to claim 1 wherein R$_1$ is a methyl group, a methoxy group or chlorine substituted on the 4-position of the phenyl group, and R$_2$ and R$_3$ each is hydrogen; R$_4$ is a dimethylaminoethyl or morpholinoethyl group; X is hydrogen or chlorine.

6. A compound according to claim 1 wherein the derivative is 2-(4-methoxyphenyl)-2,3-dihydro-5-(2-dimethylaminoethyl)-1,5-benzothiazepine-3,4(5H)-dione.

7. A method for producing a compound formula:

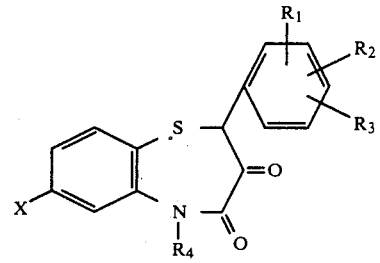

wherein R$_1$, R$_2$ and R$_3$ each independently denotes hydrogen, a halogen, a lower alkyl group, a lower alkoxy group or a hydroxy group; R$_4$ denotes a lower alkyl group, an allyl group, a lower alkoxy-alkyl group, a lower alkyl group substituted with a hydroxy group or halogen, a lower alkylaminoalkyl group or a morpholino lower alkyl group; X denotes a halogen or hydrogen and an acid salt thereof, which comprises reacting a compound of the following formula:

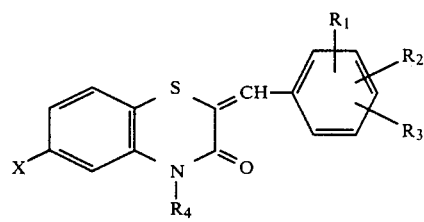

wherein R$_1$, R$_2$, R$_3$, R$_4$ and X have the same meaning as above with trimethylhalosilane, hydrogen peroxide and water.

8. A method according to claim 7 wherein R$_1$, R$_2$ and R$_3$ each is independently hydrogen, chlorine, a methyl group or a methoxy group; R$_4$ is a methyl, methoxymethyl, hydroxyethyl, chloroethyl, bromoethyl, dimethylaminoethyl or morpholinoethyl group; X is hydrogen or chlorine.

9. A method for expanding a benzothiazine ring to a benzothiazepine ring which comprises reacting a 4-substituted-2-phenyl methylidine-2H-1,4-benzothiazine-3-(4H)-one compound with trimethylhalosilane, hydrogen peroxide and water, whereby the benzothiazine ring expands to form a 2-phenyl-2,3-dihydro-5-substituted-1,5-benzothiazepine-3,4-(5H)-dione compound.

* * * * *